(12) United States Patent
Gerngross et al.

(10) Patent No.: US 9,051,593 B2
(45) Date of Patent: Jun. 9, 2015

(54) RECOMBINANT PROKARYOTES AND USE THEREOF FOR PRODUCTION OF O-GLYCOSYLATED PROTEINS

(75) Inventors: Tillman U. Gerngross, Hanover, NH (US); Grant E. Henderson, Upton, MA (US); Errik Anderson, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 111 days.

(21) Appl. No.: 13/517,348

(22) PCT Filed: Dec. 14, 2010

(86) PCT No.: PCT/US2010/060168
§ 371 (c)(1),
(2), (4) Date: Nov. 27, 2012

(87) PCT Pub. No.: WO2011/078987
PCT Pub. Date: Jun. 30, 2011

(65) Prior Publication Data
US 2013/0065274 A1    Mar. 14, 2013

Related U.S. Application Data

(60) Provisional application No. 61/288,388, filed on Dec. 21, 2009.

(51) Int. Cl.
| | | |
|---|---|---|
| *C12P 21/06* | (2006.01) | |
| *C12P 21/00* | (2006.01) | |
| *C12N 9/10* | (2006.01) | |

(52) U.S. Cl.
CPC ............. *C12P 21/005* (2013.01); *C12N 9/1051* (2013.01); *C12Y 204/01041* (2013.01)

(58) Field of Classification Search
None
See application file for complete search history.

(56) References Cited

U.S. PATENT DOCUMENTS

| | | | | |
|---|---|---|---|---|
| 5,882,902 | A | 3/1999 | Nilsson | 435/74 |
| 6,872,398 | B2 | 3/2005 | Castric et al. | 424/242.1 |
| 6,916,649 | B2 | 7/2005 | Clausen et al. | 435/252.3 |
| 7,045,337 | B2 | 5/2006 | Schultz et al. | 435/252.3 |
| 7,378,263 | B2 | 5/2008 | Schultz et al. | 435/193 |
| 2002/0001831 | A1 | 1/2002 | DeFrees et al. | 435/101 |
| 2003/0186850 | A1 | 10/2003 | Clausen et al. | 514/8 |
| 2009/0311744 | A1 | 12/2009 | DeFrees et al. | 435/69.1 |

FOREIGN PATENT DOCUMENTS

| | | |
|---|---|---|
| WO | WO 97/43405 | 11/1997 |
| WO | WO 2008/128230 | 10/2008 |

OTHER PUBLICATIONS

Lemp et al. J. Biol. Chem., 265:15606-15610, 1990.*
Rice et al., J. Biol. Chem., 265:18423-18428, 1990.*
Brokx et al. "Nuclear Magnetic Resonance-Based Dissection of a Glycosyltransferase Specificity for the Mucin MUC1 Tandem Repeat" Biochemistry 2003 42(47):13817-13825.
Cheng et al. "Characterization of a Novel Human UDP-GalNAc Transferase, pp-GalNAc-T10[1]" FEBS Letters 2002 531:115-121.
Cheng et al. "Characterization of a Novel Human UDP-GalNAc Transferase, pp-GalNAc-T15" FEBS Letters 2004 566:17-24.
Creuzenet et al. "Expression, Purification, and Biochemical Characterization of WbpP, a New UDP-GlcNAc C4 Epimerase from *Pseudomonas aeruginosa* Serotype O6" The Journal of Biological Chemistry 2000 275(25):19060-19067.
Faridmoayer et al. "Functional Characterization of Bacterial Oligosaccharyltransferases Involved in O-Linked Protein Glycosylation" Journal of Bacteriology 2007 189(22):8088-8098.
Nakamura et al. "Characterization of a Novel Polypeptide N-Acetylgalactosaminyltransferase (dGalNAc-T3) from *Drosophila*" Biological and Pharmaceutical Bulletin 2004 27(10):1509-1514.
Pratt et al. "Deconvoluting the Functions of Polypeptide N-α-Acetylgalactosaminyltransferase Family Members by Glycopeptide Substrate Profiling" Chemistry & Biology 2004 11:1009-1016.
Ramakrishnan et al. "Novel Method for in Vitro O-Glycosylation of Proteins: Application for Bioconjugation" Bioconjugate Chemistry 2007 18(6):1912-1918.
Takeuchi et al. "O-GalNAc Incorporation into a Cluster Acceptor Site of Three Consecutive Threonines. Distinct Specificity of GalNAc-transferase Isoforms" European Journal of Biochemistry 2002 269:6173-6183.
Tetaert et al. "Studies of Acceptor Site Specificities for Three Members of UDP-GalNAc:N-Acetylgalactosaminyltransferases by using a synthetic peptide mimicking the tandem repeat of MUC5AC" Carbohydrate Research 2001 333:165-171.
Wandall et al. "Substrate Specificities of Three Members of the Human UDP-N-Acetyl-α-D-galactosamine: Polypeptide N-Acetylgalactosaminyltransferase Family, GalNAc-T1, -T2 and -T3" The Journal of Biological Chemistry 1997 272(38):23503-23514.
International Search Report from PCT/US2010/060168, Feb. 8, 2011.
International Preliminary Report on Patentability from PCT/US2010/060168, Jun. 26, 2012.

\* cited by examiner

*Primary Examiner* — Nancy T Vogel
(74) *Attorney, Agent, or Firm* — Licata & Tyrrell P.C.

(57) ABSTRACT

The present invention embraces a recombinant prokaryotic host cell containing nucleic acids encoding an eukaryotic UDP-GalNAc:UDP-GalNAc polypeptide transferase and expressing an UDP-GlcNAc C-4 epimerase and methods for using the same to produce an O-glycosylated protein.

7 Claims, No Drawings

RECOMBINANT PROKARYOTES AND USE THEREOF FOR PRODUCTION OF O-GLYCOSYLATED PROTEINS

INTRODUCTION

This application is a U.S. National Stage Application of PCT/US2010/060168 filed Dec. 14, 2010 which claims benefit of priority to U.S. Provisional Application Ser. No. 61/288,388, filed Dec. 21, 2009, the contents of each of which are incorporated herein by reference in their entirety.

BACKGROUND OF THE INVENTION

Protein glycosylation is a fundamental process in living organisms. Analysis of the frequency of glycosylation has predicted that more than half of all proteins in nature will eventually be identified as glycoproteins. Without these added carbohydrates, the function of many proteins is aberrant. Complex carbohydrates are involved in cellular communication via cell/cell contact, metastasis (the spread of cancer cells through the body), viral and bacterial adhesion, and binding of toxins to cells. Understanding the roles of carbohydrate biology is crucial to basic health research and to the pharmaceutical industry.

Although protein glycosylation is rare in *Escherichia coli*, it is a common phenomenon in other bacteria. Bacteria can tolerate the manipulation of their glycosylation systems and are therefore useful for glycoengineering. In this respect, the use of bacteria to produce O-glycosylated recombinant proteins is described in Faridmoayer, et al. ((2007) *J. Bacteriol.* 189(22)8088) and U.S. Pat. No. 6,872,398 ('398 patent). Specifically, the '398 patent teaches a multivalent vaccine against Gram-negative bacterial infections composed of heterologously glycosylated pili from *Pseudomonas aeruginosa*. To produce this vaccine, the '398 patent teaches the introduction into a Gram-negative bacterium, of a vector containing pilA, the pilin structural gene from *P. aeruginosa*, and pilO, the gene from *P. aeruginosa* coding for the protein responsible for the attachment of the O-antigen repeating unit to the pilin subunit. Once expressed, PilO adds the O-antigen repeating unit of the host Gram-negative bacterium to the pilin protein PilA. The O-glycosylated pilin is then purified from a culture of the transformed bacteria. However, PilO is unable to transfer glycans to internal glycosylation sites in proteins to be glycosylated thereby limiting its use.

WO/1997/043405 also suggests the use of bacteria to express human UDP-N-acetyl-α-D-galactosamine:polypeptide N-acetylgalactosaminyltransferase (GalNAc-T3) and the production of glycosylated polypeptides having particular enzymatic, immunogenic, or other biological or physical properties. Similarly, U.S. Pat. No. 6,916,649 suggests the use of bacteria to express human UDP-galactose: β-N-acetylglucosamine β-1,4-galactosyltransferase (GalNAc-T2). U.S. Pat. Nos. 7,045,337 and 7,378,263 also generally refer to the expression of an N-acetyl-galactosamimidase, a transglycosylase, or a serine-glycosylhydrolase to glycosylate amino acids in bacteria. Furthermore, enzymatic synthesis for the preparation of GalNAc-α-linked compounds using glycosyltransferases and glycosidases obtained from natural sources or from recombinant cells is suggested in U.S. Pat. No. 5,882,902.

Likewise, WO/2008/128230 teaches the production of reference glycoproteins such as antibodies, fusion proteins and hormones having defined glycan structures. This reference teaches the use of *E. coli* and expression of enzymes that cleave polysaccharides such as degrading enzymes, enzymes that add monosaccharides to a glycan structure, enzymes that remove a component of a monosaccharide, enzymes that add a component to a monosaccharide and enzymes that convert a chemical unit into a different chemical unit.

While O-glycosylation of therapeutic proteins in prokaryotes has been suggested by co-expressing the therapeutic protein and a heterologous glycosyltransferase that transfers a sugar moiety to an amino acid acceptor on the therapeutic protein (US 2009/0311744), O-GalNAc-T has been suggested to form inactive inclusions when expressed in *E. coli* (Ramakrishnan, et al. (2007) *Bioconjug. Chem.* 18(6):1912-8). In this respect, improved methods for expression in prokaryotes are needed. Moreover, suitable donor substrates need to be provided to the above-described cells in order to synthesize glycoproteins.

SUMMARY OF THE INVENTION

The present invention features a recombinant prokaryotic host cell containing nucleic acids encoding an eukaryotic UDP-GalNAc:UDP-GalNAc polypeptide transferase and expressing an UDP-GlcNAc C-4 epimerase. In one embodiment, the UDP-GlcNAc C-4 epimerase is an exogenous UDP-GlcNAc C-4 epimerase. In another embodiment, the prokaryotic host cell further contains nucleic acids encoding one or more additional glycosyltransferases or glycosidases. In a further embodiment, the prokaryotic host cell further contains nucleic acids encoding a target protein or peptide having one or more O-glycosylation sites. Methods for using the recombinant prokaryotic host cell to produce an O-glycosylated protein or peptide is also provided.

DETAILED DESCRIPTION OF THE INVENTION

It has now been shown that a bacterial host cell expressing active UDP-GalNAc:UDP-GalNAc polypeptide transferase and active UDP-GlcNAc C-4 epimerase can efficiently O-glycosylate a recombinant mammalian protein expressed by the same host cell. As is known in the art, O—O-glycosylation is the linkage of an oligosaccharide to a peptide backbone through threonine, serine, hydroxyproline, tyrosine, or other hydroxy-containing amino acids. In so far as endogenous UDP-GlcNAc is a precursor to cell wall synthesis, the host cell contains an available pool of donor substrate that is epimerized to UDP-Gal-NAc via the UDP-GlcNAc C-4 epimerase, which, in turn, serves as a donor substrate for the UDP-GalNAc:UDP-GalNAc polypeptide transferase. Accordingly, the present invention embraces an efficient in vivo method for producing O-glycosylated proteins or peptides using a prokaryotic host cell coexpressing UDP-GalNAc:UDP-GalNAc polypeptide transferase and UDP-GlcNAc C-4 epimerase.

Any desired target protein or peptide can be O-glycosylated in accordance with the present invention. In particular, it is contemplated that the instant invention finds application in preparing target proteins or peptides for research and therapeutic use, as well as in preparing modified target proteins or peptides, which exhibit prolonged serum half-life and/or modified immunogenicity and/or improved pharmacological properties. Proteins and peptides with known or predicted O-glycosylation sites include, but are not limited to, mucin, high-molecular-weight kininogen, apolipoprotein, choriogonadotropin beta chain, corticotropin/lipotropin, human plasminogen, kallikrein, kappa-casein, leukosialin, interleukin-2, hemopexin, granulocyte-macrophage colony-stimulating factor, glycophorin C, lithostathine, interferon alpha-2, and lymphotoxin. A comprehensive list of glycoproteins with O-linked glycosylation sites is available from the O-GLYC-BASE database (Gupta, et al. (1999) *Nucleic Acids Res.* 27(1):370-2). Additional O-glycosylated proteins or peptides can be identified using the NetOGlyc Server, which produces neural network predictions of mucin type GalNAc O-glycosylation sites in mammalian proteins (Julenius, et al. (2005) *Glycobiology* 15:153-164), or other conventional methods. See, e.g., Lu, et al. (2009) *Peptides* 30(2):359-64. When a protein or peptide of interest does not contain a native O-glycosylation site or substrate, one or more O-glycosylation sites may be engineered into the protein or peptide. For example, insertion of peptide sequences containing threonine or serine have been shown to undergo glycosylation in the presence of UDP-GalNAc:polypeptide N-acetylgalactosaminyltransferase and UDP-GalNAc in a sequence-dependent manner (see, e.g., O'Connell, et al. (1992) *J. Biol. Chem.* 267(35): 25010-25018). For example, the substrate Pro-Pro-Asp-Ala-Ala-Thr-Ala-Ala-Pro-Leu-Arg (SEQ ID NO:1) is known as a suitable acceptor of GalNAc. Additional O-glycosylation sites are known in the art and described, e.g., in U.S. Pat. No. 5,843,713, incorporated herein by reference, and U.S. Patent Application No. 2009/0169509.

To produce an O-glycosylated protein or peptide in accordance with the instant invention, a target protein having an O-glycosylation site is contacted with a recombinant prokaryotic host cell containing and expressing nucleic acids encoding an eukaryotic UDP-GalNAc:UDP-GalNAc polypeptide transferase and UDP-GlcNAc C-4 epimerase so that the protein is O-glycosylated. In one embodiment, contact of the target protein or peptide with the recombinant prokaryotic host cell is achieved by adding the target protein or peptide to the media or batch feeding. In this respect, the target protein or peptide is taken up by the prokaryotic host cell (e.g., either passively or actively by endogenous or exogenous transporters) and O-glycosylated by the recombinant eukaryotic UDP-GalNAc:UDP-GalNAc polypeptide transferase expressed by the host cell. In another embodiment, the step of contacting the target protein or peptide with the recombinant prokaryotic host cell is achieved by expressing the target protein or peptide in the prokaryotic host cell. Any conventional method for expressing recombinant proteins or peptides can be employed and exemplary techniques are described herein.

As is conventional in the art, UDP-GalNAc:UDP-GalNAc polypeptide transferases, also referred to as uridine diphosphoacetylgalactosamine-glycoprotein acetylgalactos-aminyltransferase (GalNAc-Ts, EC 2.4.1.41), initiate mucin-type O-linked glycosylation by catalyzing the transfer of GalNAc (N-acetylgalactosamine) to serine and threonine residues on target proteins. GalNAc-T proteins are characterized by an N-terminal transmembrane domain, a stem region, a lumenal catalytic domain containing a GT1 motif and Gal/GalNAc transferase motif, and a C-terminal ricin/lectin-like domain. There are at least 21 different GalNAc-Ts (GalNAc-T1 to -T21) and any suitable UDP-GalNAc:UDP-GalNAc polypeptide transferase can be expressed by the prokaryotic host cell according to the present invention. Exemplary transferases include, but are not limited to, eukaryotic N-acetyl-galactosaminyltransferase, GalNAc-T1, GalNAc-T2 and GalNAc-T3 proteins. These proteins are known in the art and the amino acid sequences of these proteins are readily available under GENBANK Accession Nos. NP_065207 (human GalNAc-T1), NP_803485 (bovine GalNAc-T1), NP_038842 (mouse GalNAc-T1), NP_077349 (rat GalNAc-T1), NP_001006381 (chicken GalNAc-T1), NP_608906 (Drosophila GalNAc-T1), NP_004472 (human GalNAc-T2), XP_873281 (bovine GalNAc-T2), NP_644678 (mouse GalNAc-T2), XP_238057 (rat GalNAc-T2), XP_419581 (chicken GalNAc-T2), NP_608773 (Drosophila GalNAc-T2), NP_004473 (human GalNAc-T3), XP_615555 (bovine GalNAc-T3), NP_056551 (mouse GalNAc-T3), NP_001015032 (rat GalNAc-T3), and XP_422023 (chicken GalNAc-T3). In one embodiment, the GalNAc-T employed contains the active site of mature GalNAc-T. In another embodiment, the GalNAc-T lacks the C-terminal ricin/lectin-like domain. In a particular embodiment, the GalNAc-T employed lacks a membrane localization signal.

Likewise, any suitable UDP-GlcNAc C-4 epimerase, also referred to as uridine diphosphate N-acetylglucosamine-4-epimerase (EC 5.1.3.7), can be expressed by the prokaryotic host cell of the invention. UDP-GlcNAc C-4 epimerase catalyzes the reaction: UDP-N-acetyl-D-glucosamine→UDP-N-acetyl-D-galactosamine. Epimerases from *Bacillus* (Soldo, et al. (2003) *Gene* 319:65-69), *Campylobacter* (Linton, et al. (2005) *Mol. Microbiol.* 55(6):1695-703; Kelly, et al. (2006) *J. Bacteriol.* 188(7):2427-2434; Namdjou, et al. (2007) *Adv. Synth. Catal.* 349(3)), *Yersinia* (Bengoechea, et al. (2002) *J. Bacteriol.* 184(15):4277-4287), *Escherichia* (Wang, et al. (2002)0 *J. Bacteriol.* 184(10):2620-2625), and *Pseudomonas* (Blanger, et al. (1999) *Microbiology* 145 (Pt 12):3505-21; Creuzenet, et al. (2000) *J. Biol. Chem.* 275(25):19060-7; Antoine, et al. (2003) *Chembiochem* 4(5):406-12; Zhao, et al. (2000) *J. Biol. Chem.* 275(43):33252-9) sp. among others have been identified. In some embodiments, the host cell expresses an endogenous UDP-GlcNAc C-4 epimerase (e.g., certain *Pseudomonas* sp. express an endogenous epimerase). In other embodiments, the host does not express an endogenous UDP-GlcNAc C-4 epimerase and is genetically engineered to express an exogenous UDP-GlcNAc C-4 epimerase. Suitable UDP-GlcNAc C-4 epimerase proteins are known in the art and the amino acid sequences of these proteins are readily available under GENBANK Accession Nos. NP_391765 (*Bacillus subtilis*), Q8X7P7 (*E. coli*), Q3EP27 (*B. thuringiensis*), Q814Z6 (*B. cereus*), B2TYD9 (*Shigella boydii*), Q86I5 (*Giardia lamblia*), Q60109 (*Yersinia enterocolitica*), Q5FRS4 (*Gluconobacter oxydans*), ACU08940 (*Flavobacteriaceae bacterium*), AAM27817 (*Pseudomonas aeruginosa*), NP_000394 (human), NP_848476 (mouse), NP_542961 (rat), NP_612044 (*Drosophila melanogaster*), NP_596043 (*Schizosaccharomyces pombe*), and NP_001062869 (*Oryza sativa*). A UDP-GlcNAc C-4 epimerase is exogenous in the sense that it is not obtained (isolated or cloned) from the prokaryotic host cell in which it is to be coexpressed with the GalNAc-T.

As used herein, "prokaryote" and "prokaryotic cell" refer to cells which do not contain a nucleus and whose chromosomal material is thus not separated from the cytoplasm. Prokaryotes include, for example, bacteria. Prokaryotic host cells particularly embraced by the present invention include those amenable to genetic manipulation and growth in culture. Exemplary prokaryotes routinely used in recombinant protein expression include, but are not limited to, *E. coli*, *Bacillus licheniformis* (van Leen, et al. (1991) *Bio/Technology* 9:47-52), *Ralstonia eutropha* (Srinivasan, et al. (2002) *Appl. Environ. Microbiol.* 68:5925-5932), *Methylobacterium extorquens* (Belanger, et al. (2004) *FEMS Microbiol Lett.* 231(2):197-204), *Lactococcus lactis* (Oddone, et al. (2009) *Plasmid* 62(2):108-18) and *Pseudomonas* sp. (e.g., *P. aeruginosa*, *P. fluorescens* and *P. syringae*). Prokaryotic host cells can be obtained from commercial sources (e.g., Clontech, Invitrogen, Stratagene and the like) or repositories such as American Type Culture Collection (Manassas, Va.). In particular embodiments, the prokaryotic host cell is *E. coli*. The expression of recombinant proteins in *E. coli* is well-known in the art. Protocols for *E. coli*-based expression systems are found in U.S. Pat. Nos. 6,245,539, 5,606,031, 5,420,027, 5,151,511, and RE33,653, among others.

The prokaryotic cells of the invention are recombinant in the sense that they have been genetically modified for the purposes of harboring nucleic acids encoding an eukaryotic UDP-GalNAc:UDP-GalNAc polypeptide transferase and optionally an exogenous UDP-GlcNAc C-4 epimerase, and target protein or peptide to be O-glycosylated. Generally, this is achieved by isolating nucleic acid molecules encoding the protein or peptide of interest and introducing the isolated nucleic acid molecules into a prokaryotic cell.

Nucleic acid molecules encoding the proteins of interest (i.e., an eukaryotic UDP-GalNAc:UDP-GalNAc polypeptide transferase and optionally an exogenous UDP-GlcNAc C-4 epimerase, and a target protein or peptide) can be isolated using any conventional method. For example, the nucleic acid molecules encoding the proteins or peptides disclosed herein can be obtained as restriction fragments or, alternatively, obtained as polymerase chain reaction amplification products. Techniques for isolating nucleic acid molecules encoding proteins of interest are routinely practiced in the art and discussed in conventional laboratory manuals such as Sambrook and Russell (Molecular Cloning: A Laboratory Manual, 3rd Edition, Cold Spring Harbor Laboratory press (2001)) and Ausubel et al. (Short Protocols in Molecular Biology, 52 edition, Current Protocols (2002)).

To facilitate the expression of proteins (including enzymes) or peptides in the prokaryotic host cell, the isolated nucleic acid molecules encoding the proteins or peptides of interest are incorporated into one or more expression vectors. Expression vectors compatible with various prokaryotic host cells are well-known and described in the art cited herein. Expression vectors typically contain suitable elements for cloning, transcription and translation of nucleic acids. Such elements include, e.g., in the 5' to 3' direction, a promoter (unidirectional or bidirectional), a multiple cloning site to operatively associate the nucleic acid molecule of interest with the promoter, and, optionally, a termination sequence including a stop signal for RNA polymerase and a polyadenylation signal for polyadenylase. In addition to regulatory control sequences discussed herein, the expression vector can contain additional nucleotide sequences. For example, the expression vector can encode a selectable marker gene to identify host cells that have incorporated the vector. Nucleic acids encoding a selectable marker can be introduced into a host cell on the same vector as that containing the nucleic acid of interest or can be introduced on a separate vector. Cells stably transfected with the introduced nucleic acid can be identified by drug selection (e.g., cells that have incorporated the selectable marker gene will survive, while the other cells die). Expression vectors can be obtained from commercial sources or be produced from plasmids routinely used in recombinant protein expression in prokaryotic host cells. Exemplary expression vectors include, but are not limited to pBR322, which is the basic plasmid modified for expression of heterologous DNA in *E. coli*; RSF1010 (Wood, et al. (1981) *J. Bacteriol.* 14:1448); pET3 (Agilent Technologies); pALEX2 vectors (Dualsystems Biotech AG); and pET100 (Invitrogen).

The regulatory sequences employed in the expression vector may be dependent upon a number of factors including whether the proteins of interest are to be constitutively expressed or expressed under inducible conditions (e.g., by an external stimulus such as IPTG). In addition, the proteins being expressed by the prokaryotic host cell can have the same regulatory sequences or different regulatory sequences. When the regulatory sequences are different, the proteins can be expressed at the same time or at different times, e.g., one protein is constitutively expressed and another is expressed under inducible conditions. By way of illustration, a glycotransferase can be constitutively expressed in combination with a glycosidase as described herein, which is only expressed under inducible conditions. In addition, proteins expressed by the prokaryotic host cell may be tagged (e.g., his6-, FLAG- or GST-tagged) to facilitate detection, isolation and/or purification.

Vectors can be introduced into prokaryotic host cells via conventional transformation techniques. Such methods include, but are not limited to, calcium chloride (Cohen, et al. (1972) *Proc. Natl. Acad. Sci. USA* 69:2110-2114; Hanahan (1983) *J. Mol. Biol.* 166:557-580; Mandel & Higa (1970) *J. Mol. Biol.* 53:159-162), electroporation (Shigekawa & Dower (1988) *Biotechniques* 6:742-751), and those described in Sambrook et al. (2001) supra. For a review of laboratory protocols on microbial transformation and expression systems, see Saunders & Saunders (1987) *Microbial Genetics Applied to Biotechnology Principles and Techniques of Gene Transfer and Manipulation*, Croom Helm, London; Puhler (1993) *Genetic Engineering of Microorganisms*, Weinheim, N.Y.; Lee, et al. (1999) *Metabolic Engineering*, Marcel Dekker, NY; Adolph (1996) *Microbial Genome Methods*, CRC Press, Boca Raton; and Birren & Lai (1996) *Nonmammalian Genomic Analysis: A Practical Guide*, Academic Press, San Diego.

As an alternative to expression vectors, it is also contemplated that nucleic acids encoding the proteins (including enzymes) and peptides disclosed herein can be introduced by gene targeting or homologous recombination into a particular genomic site of the prokaryotic host cell so that said nucleic acids are stably integrated into the host genome.

Recombinant prokaryotic host cells harboring nucleic acids encoding an eukaryotic UDP-GalNAc:UDP-GalNAc polypeptide transferase and optionally an exogenous UDP-GlcNAc C-4 epimerase, and a target protein or peptide can be identified by conventional methods such as selectable marker expression, PCR amplification of said nucleic acids, and/or activity assays for detecting the expression of the eukaryotic UDP-GalNAc:UDP-GalNAc polypeptide transferase, UDP-GlcNAc C-4 epimerase, and/or target protein or peptide. Once identified, recombinant prokaryotic host cells can be cultured and stored according to routine practices.

In addition to UDP-GalNAc:UDP-GalNAc polypeptide transferase, and optionally UDP-GlcNAc C-4 epimerase, further embodiments of this invention embrace providing the prokaryotic host cell with one or more additional glycosyltransferases to further modify the target glycoprotein and/or the core O-GalNAc glycan. For example, to incorporate a sialic acid, a sialyltransferase (e.g., alpha 2→3 sialyltransferase, alpha 2→6 sialyltransferase, or cytidine 5'-monophosphosialic acid-glycoprotein sialyltransferase) can be used. To incorporate a fucose, a fucosyltransferase (e.g., alpha 1→2 fucosyltransferse, alpha 1→3 fucosyltransferase, alpha 1→4 fucosyltransferase or alpha 1→6 fucosyltransferase) can be used. Glycosyltransferases for incorporating galactose and GlcNAc include a galactosyltransferase (e.g., alpha 1→3 galactosyltransferase, beta 1→4 galactosyltransferase or beta 1→3 galactosyltransferase) and a N-acetylglucosaminyltransferase (e.g., N-acetylglucosaminyltransferase I, II or III), respectively. Examples of other enzymes which modify, add, transfer, or remove a component of a monosaccharide include, but are not limited to galactose oxidase, N-acetylneuraminate 7-0 (or 9-0) acetyl transferase, galactose-1- phosphate uridyl transferase, N-acetylglucoasamine deacetylase, L-fucose kinase, glucokinase 1, N-acetylglucosamine sulfotransferase, galactosyl sulfotransferase, N-acetylglucosamine kinase, phosphoglucomutase, N-acetylneuraminic acid phosphate synthetase, UDP-N-GlcNAc-pyrophosphorylase, UDP-glucuronate dehydrogenase, and UDP-glucose pyrophosphorylase.

Other exemplary enzymes that can be affected in a recombinant prokaryotic host cell include N-acetylglucosamine-6-phosphate 2-epimerase, CMP-Neu5Ac hydroxylase, CMP-Neu5Ac synthetase, cyclic sialic acid hydrolase, fucose-1-phosphate guanyltransferase, UDP-galaclose-4-epimerase, mannosyltransferase, UDP-N-acetylglucosamine 2-epimerase, glucose phosphate isomerase, UDP-glucuronate decarboxylase, CMP-sialic acid transporter, GDP-fucosyl transporter, UDP-galactosyl transporter and other appropriate enzymes relevant to the production and transport of sugar nucleotide substrates.

In addition to enzymes that add or transfer sugar residues to proteins, the present invention also embraces the use of one or more degradative enzymes, i.e., glycosidases. Such degradative enzymes include galactosidases (e.g., alpha-galactosidase or beta-galactosidase), sialidases (e.g., an alpha 2→3 sialidase or an alpha 2→6 sialidase), fucosidases (e.g., an alpha 1→2 fucosidase, a alpha 1→3 fucosidase, an alpha 1→4 fucosidase or an alpha 1→6 fucosidase), beta-N-acetylhexosaminidases, and alpha-N-acetylgalactosaminidases.

The sequences encoding any of the above-referenced enzymes are known in the art. Such enzymes can be added to the media or batch fed to the cell or the cell can be genetically engineered to express said enzymes to facilitate the production of the desired glycan characteristic or characteristics of target glycoproteins.

In so far as mammalian glycosyltransferases utilize nine sugar nucleotide donors: UDP-glucose, UDP-galactose, UDP-GlcNAc, UDP-GalNAc, UDP-xylose, UDP-glucuronic acid, GDP-mannose, GDP-fucose, and CMP-sialic acid (Essentials of Glycobiology (2009) Ajit Varki (ed.) 2nd ed., Cold Spring Harbor Laboratories Press), additional sugar, sugar precursors and/or sugar analogues (e.g., ketone or azide analogues) can be added to media or batch fed to cells to affect glycosynthesis. For example, activated monosaccharides (e.g., UDP-galactose, UDP-glucose, UDP-N-acetylglucosamine, UDP-xylose, GDP-mannose, GDP-fucose, CMP-N-acetylneuraminic acid, and CMP-N-acetylglycolyl-neuraminic acid), modified sugars (e.g., 2-azido galactosamine) and/or or other monosaccharide precursors (e.g., N-acetylglucosamine, glucosamine, glucose, galactose, N-acetylgalactosamine, fructose, fucose, glucose-6-phosphate, mannose-6-phosphate, mannose-1-phosphate, fructose-6-phosphate, glucosamine-6-phosphate, N-acetylglucosamine-6-phosphate, N-acetylmannosamine, N-acetylneuraminic acid-6-phosphate, fucose-1-phosphate, ATP, GTP, GDP, GMP, CTP, CDP, CMP, UTP, UDP, UMP, undine, adenosine, guanosine, cytodine, lactose, maltose, sucrose, frustose 1,6 biphosphate, 2-oxaloacetate and pyruvate) can be added to media or batch fed to cells.

Prokaryotic host cells of this invention are desired because, in contrast to the complex endogenous glycosylation processes present in eukaryotic cells, glycosylation in prokaryotes is generally limited to a few secreted proteins and is not essential to cell viability (Benz & Schmidt (2002) Mol. Microbiol. 45(2):267-276). The choice of E. coli in particular adds the potential for mutagenesis and high throughput screening in future experiments. In this simple background, it is expected that only two recombinant proteins would be needed to direct vertebrate type O-glycosylation. Specifically, UDP-GlcNAc C-4 epimerase converts naturally present UDP-GlcNAc into UDP-GalNAc and O-GalNAc-T catalyzes GalNAc addition at the appropriate serine or threonine residues of the recombinant nascent protein. The ability to produce O-glycoproteins in prokaryotes such as E. coli combined with the powerful genetic manipulation techniques available for this host will allow for the rapid creation of glycoprotein libraries and synthesis of more complex glycan structures.

The instant prokaryotic-based platform for protein modification now allows for coupling of an engineered glycosylation pathway with a subsequent chemoenzymatic labeling strategy in which the glycans are oxidized to provide a bioorthogonal aldehyde group that can react with appropriate nucleophiles for the construction of bioconjugates. This strategy can take advantage of the relaxed substrate specificity of the fungal enzyme galactose oxidase, which is capable of oxidizing Gal and GalNAc both as monosaccharides and as terminal, non-reducing components of polysaccharides (Schlegel, et al. (1968) Carbohydrate Res. 7(2):193-199). Each of the downstream modification reactions (i.e., glycan oxidation and nucleophilic addition) have been described in the literature; however, suitable recombinant glycoprotein substrates have only been produced in eukaryotic hosts (Asada, et al. (1999) Glycoconj. J. 16(7):321-326; O'Shannessy (1990) Methods Enzymol. 184:162-6; Hermanson (2008) Bioconjugate Technniques, Elsevier, Amsterdam, $2^{nd}$ edition; Bayer, et al. (1988) Anal. Biochem. 170(2):271-281; Vocadlo, et al, (2003) Proc. Natl. Acad. Sci. USA 100(16):9116-21; Solomon, et al. (1990) J. Chromatography 510:321; Poduslo, et al. (1976) J. Biol. Chem. 251(1):153-8; O'Shannessy & Quarles (1987) J. Immunol. Meth. 99(2):153-61; Osuga, et al. (1989) J. Protein Chem. 8(4):519-28; O'Shannessy, et al. (1984) Immunol. Lett. 8(5):273-7; O'Shannessy, et al. (1987) Anal. Biochem. 163(1):204-209; Morell, et al. (1966) J. Biol. Chem. 241(16):3745-9; Lee & Fortes (1985) Biochemistry 24(2):322-30; Blkova, et al. (2002) J. Chromatogr. B 770(1-2):25-34; Avigad (1985) Arch. Biochem. Biophys. 239(2): 531-537; Wilchek & Bayer (1987) Methods Enzymol. 138: 429-42; Wilchek, et al. (1980) Biochem. Biophys. Res. Commun. 92(4):1215-22; Zalipsky (1995) Bioconjug. Chem. 6(2):150-165), or in vitro using purified or partially purified enzymes (Ramakrishnan, et al. (2008) Expert Opin. Drug Deliv. 5(2):149-53; Ramakrishnan, et al. (2007) Bioconjug. Chem. 18(6):1912-81; DeFrees, et al. (2006) Glycobiology 16(9):833-43; Bulter, et al. (2001) ChemBioChem. 2(12)). A general characteristic of the studies on the modification of eukaryotic glycoproteins is that the presence of multiple oxidizable saccharide residues results in the incorporation of label molecules at a stoichiometric ratio greater than 1:1 (label/glycoprotein). The in vitro glycosylation technique provides a working system for the synthesis of homogeneously glycosylated glycoprotein precursors but these reactions have additional costs associated with the need for nucleotide sugar donors and are not as flexible in their implementation as the in vivo process disclosed herein. Many of the problems associated with eukaryotic expression and in vitro glycosylation are circumvented by the instant invention thereby fulfilling a long-felt need for a facile method of producing O-glycoproteins in an amenable prokaryotic system.

The invention is described in greater detail by the following non-limiting examples.

EXAMPLE 1

O-Glycosylation of a Mucin Reporter Protein

Vertebrate type O-glycans are desirable because of the potential for site-selectivity and the ability to incorporate a single GalNAc residue. The fact that the glycan is composed of a human sugar and linkage, specifically, GalNAcal-O-Ser/Thr, makes this modification ideal for use in therapeutic applications. Numerous O-GalNAc-Ts have been characterized and in silico screening suggests the existence of several others (Ten Hagen, et al. (2003) *Glycobiology* 13(1):1R-16R). Members of the O-GalNAc-T family have an N-terminal membrane anchor, an internal catalytic domain and in many cases, a C-terminal lectin domain. Activity against nascent proteins is generally maintained upon removal of the membrane anchor and/or lectin domain; however removal of the lectin domain abolishes activity against glycoproteins (Wandall, et al. (2007) *Glycobiology* 17(4):374-87). The characterization of O-GalNAc-Ts often includes recombinant expression in a eukaryotic host such as *P. pastoris*, COS-7, or *Drosophila* and subsequent assessment of activity against a panel of synthetic polypeptides in vitro (Wandall, et al. (1997) *J. Biol. Chem.* 272(38):23503-23514; Tetaert, et al. (2001) *Carbohydr. Res.* 333(2):165-71; Takeuchi, et al. (2002) *Eur. J. Biochem.* 269(24):6173-83; Brokx, et al. (2003) *Biochemistry* 42(47):13817-25; Cheng, et al. (2004) *FEBS Lett.* 566(1-3):17-24; Cheng, et al. (2002) *FEES Lett.* 531(2):115-121; Nakamura, et al. (2004) *Biol. Pharm. Bull.* 27(10):1509-14; Pratt, et al. (2004) *Chemistry & Biology* 11(7):1009-1016). The crystal structure of O-GalNAc-T I has been solved and of special importance is the presence of four conserved cysteines (Fritz, et al. (2004) *Proc. Natl. Acad. Sci. USA* 101(43):15307-15312). These residues have been shown to be essential for enzyme activity, implying their role in disulfide bond formation and protein folding.

Target sequences for certain O-GalNAc-T have been identified. For example, the hexapeptide Xaa-Xaa-Thr-Pro-Xaa-Pro (SEQ ID NO:2), wherein Xaa is a small hydrophobic amino acid, has been found to be the shortest Mucl-derived sequence capable of accepting GalNAc in an in vitro assay using O-GalNAc-T I (Yoshida, et al. (1997) *J. Biol. Chem.* 272(27):16884-16888). In subsequent studies it was found that the sequence Ala-Ala-Thr-Pro-Ala-Pro (SEQ ID NO:3) was also an efficient signal for O-glycan attachment in CHO cells expressing only endogenous O-GalNAc-Ts (Asada, et al. (1999) supra). In this respect, O-GalNAc-T II has been shown to exhibit activity toward the same substrates as O-GalNAc-T I.

To evaluate UDP-GalNAc:UDP-GalNAc polypeptide transferase activity and demonstrate the capacity for in vivo O-glycosylation, a reporter protein was created composed of a translational fusion between the C-terminus of approximately 3.5 sequential copies of the twenty amino acid tandem repeat region of mucin protein, MUC1, and the N-terminus of green fluorescent protein, GFP. Mucin proteins are secreted from mucous membranes and are extensively O-glycosylated in several mammalian tissues. The heavily glycosylated tandem repeat region has been used in previous studies demonstrating the sequence requirements of UDP-GalNAc:UDP-GalNAc polypeptide transferase. GFP was chosen because it is easily expressed in *E. coli* and can be detected by western blot analysis with commercially available antibodies. When this protein is modified by the attachment of O-linked GalNAc, it becomes a binding target for soy bean agglutinin, but the nascent protein is not recognized by this lectin.

The UDP-GalNAc:UDP-GalNAc polypeptide transferase used in this analysis was UDP-GalNAc:UDP-GalNAc polypeptide transferase II, however other UDP-GalNAc:UDP-GalNAc polypeptide transferase family members will function in the same capacity to transfer glycans to proteins. Upon heterologous expression of UDP-GalNAc:UDP-GalNAc polypeptide transferase in *E. coli*, transferase activity was detected in whole cell lysates via an in vitro assay, and the ability to O-glycosylated proteins was later confirmed by the UDP-GalNAc:UDP-GalNAc polypeptide transferase-dependent glycosylation of the mucin-based reporter protein in vivo. Specifically, cells lacking UDP-GalNAc:UDP-GalNAc polypeptide transferase but containing UDP-GlcNAc C-4 epimerase were not able to glycosylate the reporter protein, whereas cells containing both UDP-GalNAc:UDP-GalNAc polypeptide transferase and UDP-GlcNAc C-4 epimerase were able to glycosylate the reporter as indicated by reduced electrophoretic mobility in SDS-PAGE and binding by GalNAc-specific lectins such as soy bean agglutinin.

The UDP-GlcNAc C-4 epimerase used in this analysis was WbpP from *P. aeruginosa*. While not essential to the practice of this invention, this protein was codon-optimized for expression in *E. coli*. Epimerase activity was detected in whole cell lysates via an in vitro assay and later confirmed by the wbpP-dependent glycosylation of the mucin-based reporter protein. Cells lacking UDP-GlcNAc C-4 epimerase but containing UDP-GalNAc:UDP-GalNAc polypeptide transferase were not able to glycosylate the reporter protein whereas cells containing both UDP-GlcNAc C-4 epimerase and UDP-GalNAc:UDP-GalNAc polypeptide transferase were able to glycosylate the reporter as indicated by reduced electrophoretic mobility in SDS-PAGE and binding by GalNAc-specific lectins such as soy bean agglutinin.

Hydroxyl groups present on sugar molecules can be oxidized to carbonyls either by treatment with periodic acid or through the use of various sugar oxidases. Nearly any glycan is compatible with periodic acid-schiff (PAS) labeling; however, the harsh reaction conditions would be expected to produce multiple aldehydes per glycan and degrade amino acid side chains (Clamp & Hough (*Biochem. J.* 94:17-24). PAS labeling of sialic acid moieties can occur under milder conditions, but like UDP-GalNAc, CMP-NANA is not produced in non-pathogenic *E. coli* strains. Furthermore, sialyltransferases catalyze transfer to glycans rather than peptides so they would have to be present as secondary transferases in a more complex system. The ability to oxidize the glycan moiety without affecting the protein component renders enzymatic methods preferable to periodic acid treatment of glycoproteins when the product is to be used in a therapeutic application. Galactose oxidase is a commercially available sugar oxidase that has been reported to be able to utilize glycopeptide substrates containing terminal Gal and GalNAc residues. Accordingly, it is expected that the glycosylated reporter protein can be oxidized by treatment with galactose oxidase and modified at the resulting aldehyde by contact with an appropriately functionalized ligand (e.g., EZ-Link-Biotin-PEG4-Hydrazide and aminooxy functionalized PEG). Aminooxy-functionalized poly(ethylene glycol) is an appropriate nucleophile because the aminooxy group remains nucleophilic at relatively low pH. The ability to conduct the reaction at pH<7 allows for greater specificity and reduces the potential for side reactions involving nucleophilic attack by amines.

What is claimed is:

1. A recombinant prokaryotic host cell comprising nucleic acids encoding an eukaryotic UDP-GalNAc:UDP-GalNAc polypeptide transferase, one or more exogenous glycosidases, and an UDP-GlcNAc C-4 epimerase, wherein the one or more exogenous glycosidases are expressed under inducible conditions and wherein the one or more exogenous glycosidases comprise galactosidases, sialidases, fucosidases or alpha-N-acetylgalactosaminidases.

2. The recombinant prokaryotic host cell of claim 1, wherein the UDP-GlcNAc C-4 epimerase is an exogenous UDP-GlcNAc C-4 epimerase.

3. The recombinant prokaryotic host cell of claim 1, further comprising nucleic acids encoding one or more glycosyltransferases.

4. The recombinant prokaryotic host cell of claim 1, further comprising a nucleic acid molecule encoding a target protein or peptide having one or more O-glycosylation sites.

5. A method for producing an O-glycosylated protein or peptide comprising contacting a target protein or peptide having one or more O-glycosylation sites with the recombinant prokaryotic host cell of claim 1 so that the target protein or peptide is O-glycosylated.

6. The method of claim 5, wherein the step of contacting the target protein or peptide with the recombinant prokaryotic host cell comprises expressing the target protein or peptide in the prokaryotic host cell.

7. The method of claim 5, further comprising contacting the target protein or peptide having one or more O-glycosylation sites with a galactose oxidase.

* * * * *

SEQUENCE LISTING

```
<160> NUMBER OF SEQ ID NOS: 3

<210> SEQ ID NO 1
<211> LENGTH: 11
<212> TYPE: PRT
<213> ORGANISM: Artificial sequence
<220> FEATURE:
<223> OTHER INFORMATION: Synthetic peptide

<400> SEQUENCE: 1

Pro Pro Asp Ala Ala Thr Ala Ala Pro Leu Arg
1               5                   10

<210> SEQ ID NO 2
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: Xaa denotes a small hydrophobic amino acid
      residue
<220> FEATURE:
<221> NAME/KEY: MISC_FEATURE
<222> LOCATION: (5)..(5)
<223> OTHER INFORMATION: Xaa denotes a small hydrophobic amino acid
      residue

<400> SEQUENCE: 2

Xaa Xaa Thr Pro Xaa Pro
1               5

<210> SEQ ID NO 3
<211> LENGTH: 6
<212> TYPE: PRT
<213> ORGANISM: Artificial sequence
<220> FEATURE:
<223> OTHER INFORMATION: Synthetic peptide

<400> SEQUENCE: 3

Ala Ala Thr Pro Ala Pro
1               5
```